United States Patent [19]

Göransson-Dahlander et al.

[11] 4,172,093
[45] Oct. 23, 1979

[54] PHARMACODYNAMICALLY ACTIVE INDAN DERIVATIVES

[75] Inventors: Barbro K. Göransson-Dahlander, Farsta; Nils Å. Jönsson, Södertälje; Ferenc Merényi, Täby, all of Sweden

[73] Assignee: AB Kabi, Stockholm, Sweden

[21] Appl. No.: 343,129

[22] Filed: Mar. 20, 1973

[30] Foreign Application Priority Data

Mar. 24, 1872 [SE] Sweden .................. 3905/72

[51] Int. Cl.² ........................... C07C 87/28
[52] U.S. Cl. ................... 260/570.8 R; 544/230; 544/398; 544/403; 260/326.8; 260/501.1; 260/558 R; 260/566 A; 260/566 AR; 260/578; 260/590 FA; 562/492; 424/250; 424/267; 424/274; 424/316; 424/330; 546/15; 546/205; 546/206
[58] Field of Search .................. 260/570.8 R

[56] References Cited
U.S. PATENT DOCUMENTS

| | | | |
|---|---|---|---|
| 3,308,157 | 3/1967 | Robertson et al. | 260/570.8 X |
| 3,419,560 | 12/1968 | Beronstein et al. | 260/570.8 X |
| 3,505,404 | 4/1970 | Petersen et al. | 260/570.8 |
| 3,657,440 | 4/1972 | Werner | 260/570.8 X |

*Primary Examiner*—Robert V. Hines
*Attorney, Agent, or Firm*—Brumbaugh, Graves, Donohue & Raymond

[57] ABSTRACT

The present invention relates to new pharmacodynamically active compounds of the general structure

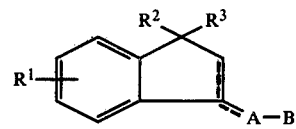

as well as the corresponding amine oxides, quarternary ammonium compounds and salts with physiologically acceptable acids. In formula I $R^1$ signifies hydrogen, halogen or alkoxy radicals having 1-3 carbon atoms, $R^2$ and $R^3$ signify alkyl radicals having 1-3 carbon atoms, which togetner with the carbon atom, to which they are connected, may form a ring, A either signifies a possibly lower alkyl substituted ethylene, trimethylene or tetramethylene group, in which case D is a group

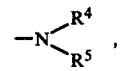

wherein $R^4$ and $R^5$ individually signify hydrogen or alkyl groups having 1-4 carbon atoms, or together with the nitrogen atom form a heterocyclic ring, which in addition to said nitrogen atom may contain an oxygen atom or possibly lower alkylated amino group, or A and B taken together signify a piperidino- or N-lower alkyl-piperidino group, which is connected to an indene residue in 4-position, and the broken lines signify a double bond in either endo- or exo position.

21 Claims, No Drawings

PHARMACODYNAMICALLY ACTIVE INDAN DERIVATIVES

In those cases where the compounds of formula I may occur as optical antipodes the invention comprises the racemic mixture as well as each of the components separately. The lower alkyl groups contain up to 6 carbon atoms, preferably 1–3 carbon atoms. The polymethylene group of the substituent A is preferably an ethylene or a trimethylene group, which may be lower alkyl substituted. The substituent $R^1$ is preferably located in the 5-position. When $R^4$ and $R^5$ form a hetercyclic ring, said ring is preferably 5-, 6- or 7-membered. Examples of suitable hetercyclic groups are the pyrrolidino and piperidino groups as well as a possibly $N^4$-lower alkylated piperazino group.

Examples of especially interesting subgroups of the new compounds of formula I are those, wherein $R^2$ and $R^3$ together with the carbon atom, to which they are bonded, form a carbocyclic ring, especially the cyclopentane ring, and further such compounds, wherein $R^1$ signifies halogen, especially chlorine or fluorine.

As examples of interesting compounds of formula I the following may be mentioned:

3'-β-Aminoethyl-spiro(cyclopentane-1,1'-indene),
3'-β-Methylaminoethyl-5'-chloro-spiro(cyclopentane-1,1'-indene)
3'-β-Methylaminoethyl-5'-fluoro-spiro(cyclopentane-1,1'-indene)
3'-β-Dimethylaminoethyl-5'-chloro-spiro(cyclopentane-1,1'-indene)
3'-β-Dimethylaminoethyl-5'-fluoro-spiro(cyclopentane-1,1'-indene)
1,1-Dimethyl-3-γ-dimethylaminopropylindene
3'-γ-Dimethylaminopropyl-spiro(cyclohexane-1,1'-indene)
3'-β-Methylaminoethyl-spiro(cyclopentane-1,1'-indene)
3'-β-Dimethylaminoethyl-spiro(cyclopentane-1,1'-indene)
3'-γ-Dimethylaminopropyl-spiro(cyclopentane-1,1'-indene)-N-oxide
3'-γ-Dimethylaminopropyl-spiro(cyclohexane-1,1'-indene)-N-oxide
3'-γ-Methylaminopropyl-spiro(cyclopentane-1,1'-indene)
3'-γ-Dimethylaminopropyl-5'-fluoro-spiro(cyclopentane-1,1'-indene)
3'-α-Methyl-β-dimethylaminoethyl-spiro(cyclopentane-1,1'-indene)
3'-β-Methylaminoethylidene-spiro(cyclopentane-1,1'-indan)
3'-β-Dimethylaminoethylidene-spiro(cyclopentane-1,1'-indan)
3'-β-Methylaminoethyl-5'-chloro-spiro(cyclopentane-1,1'-indene)
3'-β-Dimethylaminoethylidene-5'-chloro-spiro(cyclopentane-1,1'-indane)
3'-β-Aminoethylidene-spiro(cyclopentane-1,1'-indan)

The new compounds of formula I are according to the invention prepared in a manner known per se as follows:

(1) In a compound of formula

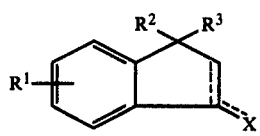

wherein $R^1$, $R^2$ and $R^3$ are as defined above, the broken lines signify a double bond in either endo- or exo-position, and X signifies a group convertible into the side chain A - B as defined above,
converting the group X into the side chain A - B, possibly under rearrangement of a possible exo-double bond into an endo-double bond, and possibly converting an exocyclic double bond in a compound of formula I obtained into an endocyclic double bond in a manner known per se, e.g. by treatment with a strong acid, or (2) reacting a substituted indanone of the general formula

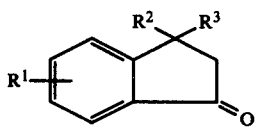

wherein $R^1$, $R^2$ and $R^3$ are as defined above, with a tertiary amino alkyl metal compound, and then hydrolyzing the adduct obtained and splitting off water from the intermediarily formed indanol.

As examples of suitable groups X which can be converted into the side chain A - B by conventional methods, the following may be mentioned: Cyanoalkyl, carbamoylalkyl, N-mono- and N,N-disubstituted carbamoylalkyl, nitroalkyl, oximinoalkyl, iminoalkyl or alkoxycarbonylaminoalkyl groups, and the conversion into compounds of formula I is performed by reduction and/or hydrolysis.

Especially suitable starting materials are unsaturated acids of the formula

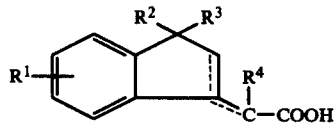

wherein $R^1$, $R^2$, $R^3$ and the broken lines are as defined above and $R^4$ signifies hydrogen or lower alkyl.

If $R^4$=H or lower alkyl said compounds are easily obtained from the corresponding substituted indanones by reaction with bromoacetic acid- or α-bromoalkanoic acid esters according to Reformatsky, followed by dehydration and hydrolysis and, if $R^4$=H, by condensation of the indanone with malonic acid or malonic acid esters and decarboxylation of the product, possibly after ester hydrolysis. According to a variant of the last mentioned process the indanone is condensed with cyano acetic acid, in which case the corresponding unsaturated cyano acetic acid derivative is formed, which is decarboxylated to the corresponding nitrile, which is either reduced to a primary amine of formula I or hydrolysed into carboxylic acid. The carboxylic acids are transformed in a manner known per se into amides which after reduction yield the desired amines of formula I.

In those cases, where X is a cyanoalkyl-, a nitroalkyl-, an oximinoalkyl- or an iminoalkyl group the conversion into the compounds I is obtained in a manner known per se by reduction. In this case the reduction agent of choice is in the first place catalytically activated hydrogen gas and the reaction is carried out in the presence of a catalyst such as platinum, a palladium or a nickel catalyst, preferably in a solvent such as water or a lower alcohol such as methanol or ethanol and at a temperature, which is preferably chosen between 20° and 150° C. and at a hydrogen pressure which is preferably chosen between atmospheric pressure and 100 atg. Another method is to reduce by means of a complex metal hydride such as a sodium borohydride or lithium aluminium hydride in an inert solvent, which can be for example ether, dioxan or tetrahydrofurane. The last-mentioned method is also preferably used in those cases, where X is a carbamoylalkyl group (B-CO-alkyl wherein B is as defined above). In those cases where X is an alkoxycarbonyl aminoalkyl group such as an ethoxycarbonyl or a methoxycarbonyl aminoalkyl group the conversion into the compounds I can be obtained by hydrolysis with an acid, preferably a mineral acid such as hydrochloric acid or sulfuric acid, or with a base, usually an alkali metal hydroxide such as a sodium or potassium hydroxide solution. In this case there is obtained under decarboxylation the compound I, in which the side chain A - B consists of the aminoalkyl group of the alkoxycarbonyl aminoalkyl group. As an alternative the alkoxycarbonyl aminoalkyl group can be converted to the corresponding N-methyl-aminoalkyl group by reduction, preferably by means of complex metal hydrides as described above.

As an alternative the group X can be a reactively esterified hydroxyalkyl group or a phosphoniumalkyl group, e.g. a halogenalkyl-, a sulphonyloxyalkyl- or a triarylphosphonium halogenidalkyl group, said intermediates being converted into the corresponding compounds of formula I or acyl derivatives thereof in a manner known per se by reaction with an amine or an alkali metal salt or an acyl-derivative thereof, e.g. a phtalyl derivative. The acyl-derivative can then be converted to the free amine I in a manner known per se.

As halogen groups in the first place chlorine and bromine compounds can be used. The sulphonyloxy derivatives are preferably methanesulphonyloxy, benzenesulphonyloxy, toluenesulphonyloxy or naphtalensulphonyloxy compounds.

In the preparation of the indene derivatives of formula I the synthesis can possibly be carried out in two steps, and in this case the unsaturated indanyliden compound is initially prepared and said compound is then converted into the corresponding indene derivative, e.g. by treatment with a strong acid.

The organometallic compounds used by the process (2) are preferably Grignard-compounds such as halogenmagnesium compounds, especially chloromagnesium compounds, but also alkali metal compounds, especially lithium compounds, can be used. Said compounds are reacted in a manner known per se with an indanone of formula III, whereafter the adduct formed is hydrolysed and dehydrated. The reaction with the Grignard-reagent is carried out in an inert solvent such as ether, dioxan or tetrahydrofuran, and the hydrolysis is preferably obtained by addition of an acid or an ammonium chloride solution.

The reactions may, of course, also be carried out by firstly preparing a lower alkylated amine derivative, a primary amine or a secondary amine, which may then be alkylated in conventional manner to the desired secondary or tertiary amine or quarternary ammonium compound. Furthermore, a prepared tertiary amine can also be dealkylated to the corresponding secondary amine.

If $R^1$ signifies halogen or alkoxy groups, said groups can either be present in the starting material or be introduced at a suitable stage of the reaction series by means of conventional methods.

The formed amines of formula I can, if desired, be converted to salts with physiologically acceptable acids, and the tertiary amines to the corresponding amine oxides.

Starting materials or end products, which are mixtures of optical isomers, may be split into the pure optical antipodes in a manner known per se, for instance by fractional crystallization of diastereoisomeric salts.

Some of the starting materials used by the process according to the invention are known compounds, whereas others are new. The starting materials which are new can be prepared by means of methods known per se. It may, for example, be mentioned that the compounds 1,1-dimethylindan-3-one and spiro(cyclohexane-1,1'-indan)-3'-one, which are known compounds, and spiro(cyclopentane-1,1'-indan)-3'-one, which is a valuable new starting compound, said compounds being used as starting materials in the following examples, can be prepared by heating the acid chlorides of the corresponding substituted β-phenylpropionic acids with polyphosphonic acid according to the general method disclosed by V. Seidlová and M. Protiva [Collection Szechoslovak Chem. Commun. Vol. 32. p. 2832 (1967)]. Possible halogen and alkoxy substituents can be introduced into the starting compounds by means of methods known per se, e.g. such as described in the following examples.

The new compound spiro(cyclopentane-1,1'-indan)-3'-one and corresponding halogen, nitro and lower alkoxy derivatives, which can be illustrated by means of the following general structure formula

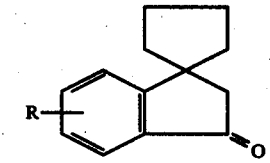

wherein R signifies halogen, especially fluorine or chlorine, alkoxy having 1–3 carbon atoms or nitro, and the corresponding ketoximes, have proved to be especially interesting intermediates in the preparation of valuable end compounds especially pharmacodynamically active compounds. As mentioned above it is true that it is possible to prepare the new intermediates of formula V by means of the above indicated method known per se, but it is difficult to prepare the 1-phenyl-1-cyclopentaneacetic acid of formula

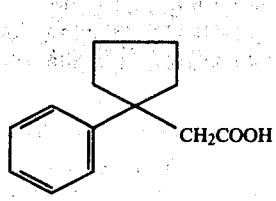

VI required as intermediate [compare Wilt. J. W. and Philips, B. H., J. Org. Chem. 25, 891 (1960)].

It has now been shown that spiro(cyclopentane-1 1'-indene), which is easily obtained from indene by alkylation with 1,4-dibromobutan, can in a simple manner and with a high yield be converted to the desired indanone of formula V by the addition of a hydrogen halogenide, preferably hydrogen chloride, and subsequent oxidation of the obtained 3'-halogen-spiro(cyclopentane-1,1'-indan), and then introducing, if desired, a halogen, nitro or lower alkyl substituent R in a manner known per se. The oxidation of the obtained 3'-halogen-(especially chloro)-spiro(cyclopentane-1,1'-indan) is preferably carried out by means of chromic acid or an acid chromate solution. The new indanones of formula V can, in addition to the preparation of the above described, new and pharmacodynamically active compounds of formula I, also be used for the preparation of other pharmacodynamically active compounds, e.g. for the preparation of new, pharmacodynamically active aminoalkyl ethers of the general formula

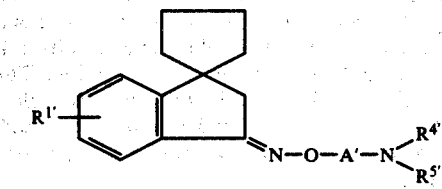

VII wherein $R^{1'}$ signifies hydrogen, halogen, lower alkoxy groups having 1–3 carbon atoms or nitro groups and $A'$ is a possibly lower alkyl substituted ethylene or trimethylene group and $R^{4'}$ and $R^{5'}$ individually signify hydrogen or alkyl groups having 1–4 carbon atoms or together with the amine nitrogen form a heterocyclic ring, which in addition to the amine nitrogen can contain an oxygen atom or a possibly lower alkylated imino group.

The indanone of formula V can be converted into the valuable end-products of formula VII by reaction with a compound of formula VIII

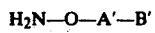 VIII wherein $A'$ is as defined above and $B'$ either is

or a group convertible thereto, whereafter $B'$, if necessary is converted to

The reaction is preferably carried out in an inert solvent such as ethanol and pyridine. The compound VIII can in this case be used as a freee base or in the form of a salt with an acid. In the latter case the reaction is carried out in the presence of an acid binding agent, e.g. sodium carbonate or pyridine. The new compounds of formula VII have pharmacodynamic properties similar to those of the new compounds of formula I.

The compounds VII can also be prepared in such a manner that the indanone V is firstly converted to the corresponding indanone oxime in conventional manner (e.g. by reaction with hydroxyl amine) and then reacting the oxime formed with a compound of formula

wherein $A'$ is as defined above and $B'$ either signifies the group

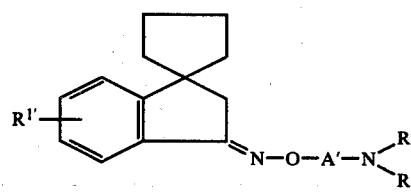

VII or a group, which may be converted into said group, and X signifies a reactively esterified hydroxy group, e.g. halogen or arylsulphonyloxy group. The reaction is preferably carried out in an inert solvent such as dimethylformamid or acetonitrile and by using the compound X—A'—B' in the form of a salt, e.g. with alkali metal ions or quarternary ammonium ions.

The new compounds of formula I according to the invention have in animal tests proved to process valuable pharmacological effects, especially on the central nervous system, which are especially manifested as an ability to counteract the effect of reserpine, an effect which in pharmacology is used as a measure of the suitability of a compound as a drug against depressions. Certain ones of the substances at the same time show other effects on the central nervous system such as a sedative effect. The compounds all together have low toxicity.

By means of conventional methods and conventional adjuvants the compounds can be transformed into suitable pharmaceutical forms of preparations, e.g. tablets or solutions, which, for example can contain between 1 and 500 mg of the active substance.

In the following table the results of tests concerning anti-reserpine effect for some specific compounds according to the invention are reported.

All experiments were carried out on albino mice, 18–25 g. The animals had free access to water except during the test period, but were not allowed to eat 4–5 hours before the experiment. The tested substances were administered orally to mice in groups of 6, at 4 dosage levels: (12.7; 40; 127 and 400 mg/kg). A control group of 6 mice receiving water was observed simultaneously.

After one hour the mice were injected intraperitoneally with 2.5 mg/kg reserpine, which had been solubilized with a few drops of glacial acetic acid. 0.5; 1; and 2 hours after the treatment with reserpine the ptosis was measured; 0 in score is given for no closure of the eye, 1 for ¼, 2 for ½, 3 for ¾ and 4 for completion closure. The score varies between 0 and 8 for each mouse (the sum of score for 2 eyes). The maximum value for 6 mice is thus 48.

The percentage of antagonism for each compound after 0.5; 1; or 2 hours for each dosage group was obtained by comparision with the score of the simultaneously observed control group. The table indicates the percentage of antagonism after 60 minutes, which is the optimal time for measuring antireserpine effect in this test system.

oughly washed with water. After drying there are obtained 1917 g of a yellow powder (yield 95%), mp. 104° C. A sample is recrystallized from N-hexane and melts at 110° C.

(c) 5'-amino-spiro(cyclopentane-1,1'-indan)-3'-one

A solution of 5'-nitro-spiro(cyclopentane-1,1'-indan)-3'-one (23.1 g; 0.1 mole) in methanol (250 ml) is hydrogenated in a shaking autoclave at about 4 atg with a Raney-nickel catalyst at 40°–60° C. The mixture is

| $R^1$ | $R^2$ | $R^3$ | A | B | Salt | Antagonism: Dosage mg/kg | | | |
|---|---|---|---|---|---|---|---|---|---|
| | | | | | | 12,7 | 40 | 127 | 400 |
| H | $CH_3$ | $CH_3$ | $-(CH_2)_3-$ | $N(CH_3)_2$ | hydrochloride | 33 | 67 | 100 | 75 |
| H | $-(CH_2)_4-$ | $=CH-CH_2-$ | | $NHCH_3$ | hydrochloride | 100 | 100 | 100 | 100 |
| H | $-(CH_2)_4-$ | $=CH-CH_2-$ | | $N(CH_3)_2$ | perchlorate | 100 | 100 | 100 | |
| H | $-(CH_2)_4-$ | $-(CH_2)_3-$ | | $NHCH_3$ | fumarate | 68 | 77 | 77 | 41 |
| H | $-(CH_2)_4-$ | $-(CH_2)_3-$ | | $N(O)(CH_3)_2$ | dihydrate | 47 | 66 | 90 | 90 |
| 5-F | $-(CH_2)_4-$ | $-(CH_2)_3-$ | | $N(CH_3)_2$ | perchlorate | 58 | 88 | 75 | 92 |
| H | $-(CH_2)_5-$ | $-(CH_2)_3-$ | | $N(CH_3)_2$ | hydrochloride | 23 | 46 | 81 | 100 |
| H | $-(CH_2)_5-$ | $-(CH_2)_3-$ | | $N(O)(CH_3)_2$ | monohydrate | 23 | 54 | 92 | 85 |
| 5-Cl | $-(CH_2)_4-$ | $-CH_2-CH_2-$ | | $NHCH_3$ | hydrochloride | 100 | 94 | 100 | 100 |
| 5-Cl | $-(CH_2)_4-$ | $=CH-CH_2-$ | | $N(CH_3)_2$ | hydrochloride | 46 | 80 | 83 | 66 |
| H | $-(CH_2)_4-$ | $=CH-CH_2-$ | | $N(O)(CH_3)_2$ | hemihydrate | 82 | 100 | 100 | 100 |
| H | $-(CH_2)_4-$ | $-CH(CH_3)CH_2-$ | | $N(CH_3)_2$ | perchlorate | 100 | 10 | — | — |
| H | $-(CH_2)_4-$ | $=CH-CH_2-$ | | $NH_2$ | hydrochloride | 100 | 100 | 100 | 100 |
| H | $-(CH_2)_4-$ | $-(CH_2)_2-$ | | $NHCH_3$ | hydrochloride | 100 | 100 | 100 | 100 |
| H | $-(CH_2)_4-$ | $-(CH_2)_2-$ | | $N(CH_3)_2$ | perchlorate | 100 | 100 | 100 | 100 |

The following examples further illustrate the invention.

EXAMPLE 1: PREPARATION OF STARTING MATERIALS (a) Spiro(cyclopentane-1,1'-indan)-3'-one Anhydrous hydrogenchloride gas is bubbled through spiro(cyclopentane-1,1'-indene) (117.5 g; 0.69 moles) until 25 g have absorbed. The temperature is held under +10° C. by cooling on an ice bath. The liquid obtained is distilled and at first a small amount of unreacted spirocyclopentaneindene passes over, followed by about 135 g (Yield 95%) 3'-chlorospiro(cyclopentane-1,1'-indan) bp 97° C./0.7 mm Hg. $n_D^{20} = 1.5625$.

To a mixture of acetic acid (75 ml), water (75 ml) and chromium trioxide (75 g; 0.75 moles) there are added dropwise under agitation 3'-chlorospiro(cyclopentane-1,1'-indan) (103 g; 0.5 moles), the temperature being held at 30°–40° C. by external cooling.

After termination of the addition the agitation is continued for another 15 minutes, whereafter the reaction mixture is pulled in ice water. The ketone is extracted immediately with ether, and then the ether solution is rapidly washed with water and saturated sodium carbonate solution. After drying with magnesium sulphate the ether is distilled off and the ketone is obtained as an oil having a boiling point of 104° C./2 mm Hg, $n_D^{25} = 1.5672$. The oxime melts at 102° C.

The above reaction can also be carried out continuously without intervening isolation of the chlorine compound.

(b) 5'-nitro-spiro(cyclopentane-1,1'-indan)-3'-one

To a chilled solution of spiro(cyclopentane-1,1'-indan)-3'-one (16.7 g; 0.09 moles) in conc. sulphuric acid (100 ml) there are added in portions under agitation a solution of potassium nitrate (10 g) in conc. sulphonic acid (30 ml). The temperature should not exceed 10°–15° C. The mixture is kept cold for 1 hour and then put on ice. The crude product is sucked off and thoroughly washed with water. After drying there are obtained 1917 g of a yellow powder (yield 95%), mp. 104° C. A sample is recrystallized from N-hexane and melts at 110° C.

chilled, the catalyst filtered off and washed with methanol, after which the filtrate is evaporated to dryness. A light yellow powder is obtained (19.5 g; yield 97%). Said powder is dissolved in 2 N hydrochloric acid and extracted with ether, and then the aqueous phase is neutralized with 2 N sodium hydroxid solution. The precipitate is filtered off, washed with water and dried, and 18.8 g of a yellow-white crystal powder is obtained. A sample is recrystallized twice from benzene and then melts at 125° C.

(d) 5'-chloro-spiro(cyclopentane-1,1'-indan)-3'-one

A mixture of 5'-amino-spiro(cyclopentane-1,1'-indan)-3'-one (20.1 g; 0.1 mole), 23% hydrochloric acid (35 ml), water (76 ml) and ice (3 g) is diazotised at about +5° C. with a solution of sodium nitrate (11 g) in water (25 ml). The clear solution is added to an ice cooled solution of copper(I)chloride(15 g) in 23% hydrochloric acid (150 ml) and water (60 ml). After agitation for 2.5 hours the mixture is heated to 100° C. for a short while and is then allowed to cool. The brown precipitate is sucked off and thoroughly washed with water. Crude yield 20 g (90%). The crude product is purified by distillation in vacuum, bp. 135°–136° C./1,5 mm Hg. A sample is crystallized from n-hexane and then melts at 54° C. The oxime melts at 140° C.

(e) 5'-fluoro-spiro(cyclopentane-1,1'-indan)-3'-one

5'-amino-spiro(cyclopentane-1,1'-indan)-3'-one (78 g; 0.39 mole) is treated for a short with 200 ml of a solution of equal volumes of conc. hydrochloric acid and water. The mixture is chilled to 10° C. and diazotised with a solution of sodium nitrate (28.5 g; 0.41 moles) in water (60 ml) at 10° C. The reaction mixture is chilled to 0° C., filtrated and dropwise treated under vigorous agitation with a solution of sodium borofluoride (59 g; 0.53 moles) in water (120 ml) at 0° ± 1°. After the addition the agitation is continued for another half an hour at 0° C., after which the precipitated diazonium fluoroborate is sucked off and washed with two 50 ml portions of ice cold water and three 50 ml portions of methanol. Drying in vacuum at 50° C. yields 97 g (82%) of a yellow product which disintegrates at about 110° C. The fluoroborate is disintegrated by heating on an oil bath to 100°-110° C. The reaction product obtained is kept at 120° C. for 10 minutes and is then allowed to cool, then treated with 1 N sodium hydroxide solution under heating until a weekly alkaline solution is obtained. Said solution is subjected to water steam distillation, whereby the desired fluoro ketone is obtained from the cooled condensate in form of colourless crystals of mp 79°-80° C. The product boils at 100°-105° C./0.1 mm Hg. The oxime melts at 156° C.

(f) 5'-hydroxy-spiro(cyclopentane-1,1'-indan)-3'-one

A mixture of 5'-amino-spiro(cyclopentane-1,1'-indan)-3'-one (20.1 g; 0.1 mole) 2 N sulphoric acid (150 ml) and ice (30 g) is diazotised at about +5° C. with a solution of sodium nitrate (11 g) in water (25 ml). The solution is filtrated and poured in boiling mixture of 100 ml of water and 10 ml of conc. sulphuric acid. The boiling is continued until the development of nitrogen gas ceases, after which the mixture is chilled and the solid, dark brown substance is filtered off. After drying there are obtained 20 g of a crude product, which is recrystallized from trichloroethylene. Yield 12 g of a light powder of mp. 145° C. 4 g of the substance can be recovered from the mother liquid by means of extraction with 2 N sodium hydroxide and subsequent precipitation with 2 N hydrochloric acid.

(g) 5'-methoxy-spiro(cyclopentane-1,1'-indan)-3'-one

A mixture of 5'-hydroxy-spiro(cyclopentane-1,1'-indan)-3'-one (20.2 g; 0.1 mole), acetone (1000 ml), anhydrous potassium carbonate (37.5 g) and methyl iodide (50 ml) is refluxed for 5-6 hours. The mixture is evaporated to dryness, after which the residue is taken up in water and trichloroethylene. The trichloroetylene solution is extracted with 2×150 ml of 2 N sodium hydroxide and dried with anhydrous magnesium sulphate. The solvent is distilled off and a yellow oil is obtained, which soon crystallizes, yield 16 g (74%). After recrystallization from n-hexane the substance melts at 80° C.

EXAMPLE 2

(a)
3'-γ-dimethylaminopropyl-5'-chloro-spiro(cyclopentane-1,1'-indene)

A solution of γ-dimethylaminopropyl chloride (24.3 g; 0.2 moles) in anhydrous tetrahydrofuran (50 ml) is added in portions to an about 60° C. hot agitated solution of magnesium flakes (4.8 g; 0.2 gram atoms) and anhydrous tetrahydrofurane (20 ml), containing 1 ml of ethylbromide and 1 crystal of iodine as reaction coupling agent. After the reaction has terminated the agitation is continued for another 15 minutes at 60° C., after which 30 ml of benzene are added and the mixture is cooled to 10°-15° C. A solution of 5'-chloro-spiro(cyclopentane-1,1'-indan)-3'-one (22.1 g; 0.1 mole) in 25 ml of tetrahydrofuran is added with such a speed that the temperature does not exceed 50° C. After said addition the mixture is refluxed for 45 minutes. The mixture is cooled to 0° C. and disintegrated with a solution of ammonium chloride (20 g) in water (100 ml). The viscous precipitate is filtered off and washed with benzene. The filtrate, which consists of two phases, is allowed to separate. The organic phase is taken away and the aqueous phase is extracted several times with benzene. The combined benzene solutions are extracted with diluted sulphoric acid (100 ml of conc. sulphoric acid to 350 ml of water). The acid aqueous phase is heated to 100° C. until volatile components have been eliminated and it is refluxed for a short while. After cooling to about 10° C. the solution is made strongly alkaline with a 40% solution of sodium hydroxide. The amine is extracted off with trichloroethylene. The extract is dried with anhydrous potassium carbonate, after which the solvent is distilled off. The amine obtained is distilled in vacuum. Yield 16.6 g (57.3%) of a light oil of bp. 157°-158°/1.5 mm Hg. $n_D^{25} = 1.5542$. The perchlorate is obtained if an ether solution of the amine is treated with perchloric acid. After crystallization from 2-propanol the salt melts at 122° C.

In an analogous manner the following substances are prepared from the respective indanones:

(b) 1,1-dimethyl-3-γ-dimethylaminopropylindene

Oil. Bp. 98°/0.8 mm. $n_D^{25} = 1.5290$. Hydrochloride, mp. 151° C.

(c) 1,1-dimethyl-3-γ-piperidinopropylindene

Oil. Bp. 134°-136° C./0.9 Hg. $n_D^{25} = 1.5212$. Hydrochloride, mp. 181°-182° C.

(d)
1,1-dimethyl-3-γ-(4-methyl-1-piperazinyl)propylindene

Oil. Bp. 145°-146° C./0.6 mm Hg. $n_D^{25} = 1.5242$. Dihydrochloride, mp. 215° C.

(e) 1,1-dimethyl-3-(N-methyl-4-piperidyl)indene

Oil. Bp. 120° C./0.8 mm Hg. Perchlorate, mp. 177° C.

(f)
3'-γ-dimethylaminopropylspiro(cyclopentane-1,1'-indene)

Oil. Bp. 140°-142° C./1.2 mm Hg. $n_D^{25} = 1.5459$. Perchlorate, mp. 112° C.

(g)
3'-γ-piperidinopropyl-spiro(cyclopentane-1,1'-indene)

Oil. Bp. 180° C./1.4 mm Hg. $n_D^{25} = 1.5392$. Hydrochloride, mp. 210° C.

(h)
3'-(N-methyl-4-piperidyl)spiro(cyclopentane-1,1'-indene)

Oil. Bp. 150° C./0.15 mm Hg. Hydrochloride. Mp. 222° C.

(i)
3'-γ-dimethylamino-β-methyl-propylspiro(cyclopentane-1,1'-indene)

Oil. Bp 116°-118° C./0.4 mm Hg. $n_D^{25} = 1.5363$. Perchlorate, mp. 170° C.

(j) 3'-γ-piperidinopropylspiro(cyclohexane-1,1'-indene)

Oil. Bp. 180°-182° C./0.18 mm Hg. $n_D^{25} = 1.5517$. Perchlorate, mp. 146°-148° C.

(k)
3'-γ-dimethylaminopropylspiro(cyclohexane-1,1'-indene)

Oil. Bp. 142°-143° C./0.6 mm Hg. $n_D^{25} = 1.5420$. Hydrochloride, mp. 190°-191° C.

(1)
3'-γ-(4-methyl-1-piperazinyl)-propylspiro(cyclohexane-1,1'-indene)

Oil. Bp. 190° C./0.9 mm Hg. $n_D^{25}=1.5512$. Dihydrochloride, mp. 230° C.

(m)
3'-(N-methyl-4-piperidyl)spiro(cyclohexane-1,1'-indene)

Oil. Hydrochloride, mp. 260° C.

(n)
3'-γ-dimethylamino-β-methyl-propylspiro(cyclohexane-1,1'-indene)

Oil. Bp. 134°–139° C./0.5 mm Hg. $n_D^{25}=1.5378$. Perchlorate, mp. 184° C.

(o)
3'-γ-dimethylaminopropyl-5'-fluoro-spiro(cyclopentane-1,1'-indene)

Oil. Bp. 136°–137° C./0.7 mm Hg. $n_D^{25}=1.5338$. Perchlorate, mp. 102° C.

(p)
3'-γ-dimethylaminopropyl-5'-methoxy-spiro(cyclopentane-1,1'-indene)

Oil. Bp. 159°–160° C./0.7 mm Hg. $n_D^{25}=1.5480$. Hydrochloride, mp. 170° C.

EXAMPLE 3

(a)
3'-β-methylaminoethylidene-spiro(cyclopentane-1,1'-indan)

A mixture of ethylbromoacetate (17.5 g; 0.105 moles) and spiro(cyclopentane-1,1'-indan)-3'-one (18.6 g; 0.1 moles) in anhydrous benzene (25 ml) is added dropwise under agitation to zinc-powder (8.0 g; 0.124 gram atoms) at 60° C. The addition is adjusted so as to maintain refluxing. After termination of the addition the agitation is continued for half an hour under heating to boiling. The mixture is allowed to cool and filtrated, after which the filtrate is treated with 10% sulphuric acid. The benzene solution is separated, washed with 5% sulphuric acid, saturated sodium carbonate solution and water. The solvent is distilled off. The oil obtained is hydrolysed with a solution of 20 g of sodium hydroxide in 50 ml of water and 50 ml of ethanol under agitation for 10 hours. The alcohol is distilled off and the distillation residue is dissolved in water, washed with ether and acidified with conc. hydrochloric acid. An oil is obtained which soon crystallizes. The hydroxy acid obtained is dehydrated by boiling with acetic acid for 10 minutes. Upon cooling spiro(cyclopentane-1,1'-indan)-3'-ylideneacetic acid crystallizes (17 g of a colourless product, yield 74%); mp. 206° C.

Spiro(cyclopentane-1,1'-indan)-3'-ylideneacetic acid (10 g; 0.044 moles) in 50 ml of thionylchloride is kept at room temperature for about 10 hours and then refluxed for 1 hours. The thionyl chloride is distilled off in vacuum and the acid chloride obtained is dissolved in ether (100 ml) and dropwise added to an agitated solution of an excess methylamine in ether under cooling. The mixture is kept over night, after which the ether and excess of methylamine is distilled off and the evaporation residue is taken up in trichloroethylene and water. The organic phase is separated, washed with water and dried over magnesium sulphate. After evaporation of the solvent and recrystallization from acetonitrile there are obtained 6.2 g (60%) of N-methylspiro(cyclopentane-1,1'-indan)-3'-yliden-acetamide of mp. 178° C.

A solution of N-methyl-spiro(cyclopentane-1,1'-indan)-3'-ylidene-acetamide (4.0 g; 0.016 moles) in anhydrous ether (100 ml) as dropwise under agitation added to a suspension of lithium aluminium hydride (1.26 g; 0.033 moles) in ether (300 ml). The mixture is refluxed for 15 hours and cooled. Saturated sodium sulphate solution is added carefully until unreacted hydride has been decomposed. The precipitate obtained is filtered off and washed with ether. The ether filtrates are dried with potassium carbonate and filtrated. Evaporation of the filtrate yields the free amine 3'-β-methylaminoethyliden-spiro(cyclopentane-1,1'-indan) as an oil. If the ether solution is instead treated with hydrogen chloride dissolved in ether the hydrochloride is obtained as colourless crystals. Yield 3.9 g (91%). After crystallization from 2-propanol the salt melts at 194° C. The neutral fumarate melts at about 200° C.

In an analogous manner the following indanylidene resp. indenylacids are prepared from the respective indanones:

1,1-dimethylindan-3-ylidene-acetic acid. A crystalline substance. Recrystallized from 2-propanol. Mp. 214° C.

Spiro(cyclohexane-1,1'-indan)-3'-ylidene-acetic acid. A crystalline substance. Recrystallized from 2-propanol. Mp. 244° C.

5'-chloro-spiro(cyclopentane-1,1'-indan)-3'-ylidene-acetic acid. A crystalline substance. Recrystallized from 2-propanol. Mp. 230° C.

α-[spiro(cyclopentane-1,1'-indene)-3'-yl]propionic acid. A crystalline substance. Recrystallized from ligroin. Mp. 88° C.

In an analogous manner the following amides are prepared from the respective indanylidene resp. indenyl acids:

N-methyl-1,1-dimethylindan-3-ylidene-acetamide. Mp. 140° C.

N-methyl-spiro(cyclohexane-1,1'-indan)-3'-ylidene-acetamide. Mp. 172°–173° C. (decomposition).

N,N-dimethyl-spiro(cyclopentane-1,1'-indan)-3'-ylidene-acetamide. Mp. 104° C.

N,N-dimethyl-1,1-dimethylindan-3-ylidene-acetamide. Mp. 64° C.

N,N-dimethyl-spiro(cyclohexane-1,1'-indan)-3'-ylidene-acetamide. Mp. 116° C.

Spiro(cyclopentane-1,1'-indan)-3'-ylidene-acetamide. Mp. 150° C.

1,1-dimetylindan-3-ylidene-acetamide. Mp. 139° C.

N-methyl-α-[spiro(cyclopentane-1,1'-indene)-3'-yl]-propionamide. Oil.

N,N-dimethyl-α-[spiro(cyclopentane-1,1'-indene)-3'-yl]-propionamide. Oil.

N,N-dimethyl-[5'-chloro-spiro(cyclopentane-1,1'-indan)-3'-ylidene]-acetamide. Mp. 162° C.

N-tert.-butyl-spiro(cyclopentane-1,1'-indan)-3-ylidene-acetamide. Mp. 214° C.

In an analogous manner the following end products are finally prepared from the corresponding amides:

(b) 1,1-dimethyl-3-β-methylaminoethylidene-indan

Hydrochloride. Mp. 192° C.

(c)
3'-β-methylaminoethylidene-spiro(cyclohexane-1,1'-indan)

Hydrochloride. Mp. 227° C.

(d)
3'-β-dimethylaminoethylidene-spiro(cyclopentane-1,1'-indan)

Hydrochloride. Mp. 200° C. Perchlorate. Mp. 170° C.

(e) 1,1-dimethyl-3-β-dimethylaminoethylidene-indan

Perchlorate. Mp. 207° C.

(f)
3'-β-dimethylaminoethylidene-spiro(cyclohexane-1,1'-indan)

Perchlorate. Mp. 124° C.

(g)
3'-β-aminoethylidene-spiro(cyclopentane-1,1'-indan)

Hydrochloride. Mp. 190° C.

(h)
3'-β-methylaminoisopropyl-spiro(cyclopentane-1,1'-indene)

Oxalate. Mp. 220° C.

(j)
3'-β-dimethylaminoisopropyl-spiro(cyclopentane-1,1'-indene)

Perchlorate. Mp. 162° C.

(k)
3'-β-methylaminoethyl-5'-chloro-spiro(cyclopentane-1,1'-indene)

Hydrochloride. Mp. 211° C.

(l)
3'-β-dimethylaminoethylidene-5'-chloro-spiro(cyclopentane-1,1'-indan)

Hydrochloride. Mp. >250° C.

(m)
3'-β-tert.-butylamino-ethylidene-spiro(cyclopentane-1,1'-indan)

Perchlorate. Mp. 196° C.

EXAMPLE 4

(a)
3'-β-trimethylammoniumethylidene-spiro(cyclopentane-1,1'-indan)-methyl sulphate Dimethyl sulphate (2.5 ml) is under shaking added to 3'-β-dimethylaminoethylidene-spiro(cyclopentane-1,1'-indan) (1.6 g; 0.007 moles) in methanol (20 ml). After about 5 minutes 450 ml of ether are added and then crystals of trimethylammonium compound are formed (2.2 g; 90%). After crystallization from 2-propanolisopropylether the salt melts at 178° C.

In an analogous manner the following quarternary ammonium salts are prepared from the corresponding tertiary amines:

(b)
1,1-dimethyl-3-β-trimethylammoniumethylidene-indan-methyl sulphate

Mp. 145° C.

(c)
3'-β-trimethylammoniumethylidene-spiro(cyclohexane-1,1'-indan)-methyl sulphate Mp. 206° C.

(d)
3'-γ-trimethylammoniumpropyl-spiro(cyclopentane-1,1'-indene) methyl sulphate Mp. 92° C.

(e) 1,1-dimethyl-3-γ-trimethylammoniumpropylindene methyl sulphate

Mp. 220° C.

(f)
3'-γ-trimethylammoniumpropyl-spiro(cyclohexane-1,1'-indene)-methyl sulphate

Mp. 169°–172° C.

(g)
3'-(N,N-dimethyl-4-piperidinium)spiro(cyclopentane-1,1-indene)-methyl sulphate Mp. 124° C.

(h)
3'-(N,N-dimethyl-4-piperidinium)spiro(cyclohexane-1,1'-indene)-methyl sulphate Mp. 174° C.

EXAMPLE 5

(a)
3'-γ-dimethylaminopropyl-spiro(cyclopentane-1,1'-indene)-N-oxide-dihydrate

3'-γ-dimethylaminopropyl-spiro(cyclopentane-1,1'-indene) (5.4 g; 0.021 moles), a 30% solution of hydrogene peroxide (2.38 g; 0.021 moles) and methanol (10 ml) are mixed and kept at room temperature for 48 hours. After evaporation to dryness in vacuum the residue is recrystallized from aceton-isopropylether. Yield 3.9 g (60%) of a white crystalline product of mp. 90° C.

In analogous manner there are prepared from a corresponding tertiaryamine:

(b)
3'-γ-dimethylaminopropyl-spiro(cyclohexane-1,1'-indene)-N-oxide-monohydrate

Mp. 90°–100° C.

(c)
3'-β-dimethylaminoethylidene-spiro(cyclopentane-1,1'-indan)-N-oxide-hemihydrate Mp. 55° C.

EXAMPLE 6

(a)
3'-γ-methylaminopropyl-spiro(cyclopentane-1,1'-indene)

To a solution of 3'-γ-dimethylaminopropyl-spiro(cyclopentane-1,1'-indene) (28.0 g; 0.11 moles) in dry benzene (120 ml) there are added dropwise during 20 minutes a solution of ethylchloroformate (18.0 g; 0.165 moles), and then the mixture is boiled for two hours, cooled, washed with 2 N hydrochloric acid and dried with anhydrous magnesium sulphate. A brown oil (26.6 g) is obtained, which is distilled in vacuum. Bp. 180° C./1.5 mm Hg. Yield 21.65 g (63%) of 3'-γ-(N-carbethoxy-N-methylamino)propyl-spiro(cyclopentane-1,1'-indene) as a yellow oil.

3'-γ-(N-carbethoxy-N-methylamino)propyl-spiro(cyclopentane-1,1'-indene) (17.3 g; 0.055 moles), acetic acid (104 ml) and 48% hydrobromic acid (37.5 ml) are mixed, boiled for 5 hours and then evaporated in vacuum. Water (200 ml) and an excess of conc. ammonia solution are added to the residue. The free amine is extracted out with ether (3×150 ml). The ether solution is dried with anhydrous potassium carbonate, and then the solvent is eliminated. The free base is obtained as a yellow oil (12.7 g; 95%). The base is dissolved in 100 ml of dry acetone and a solution of fumaric acid (6.5 g) in acetone (750 ml) is added. A precipitate is obtained, which is filtered off and recrystallized from acetone. Colourless crystals of 3'-γ-methylaminopropyl-spiro(cyclopentane-1,1'-indene) of mp. 90° C.

In an analogous manner there is prepared via the intermediate 3'-γ-(N-carbethoxy-N-methylamino)propyl-spiro(cyclohexane-1,1'-indene).

(b)

3'-γ-methylaminopropyl-spiro(cyclohexane-1,1'-indene)

Fumaric acid monoamine salt, mp. 92°–96° C.

EXAMPLE 7

3'-γ-(1-pyrrolidinyl)propyl-spiro(cyclopentane-1,1'-indene)

The Grignard reagent is prepared from γ-methoxypropyl bromide (30.6 g; 0.2 moles) and magnesium flakes (4.8 g; 0.2 gram-atoms) in tetrahydrofuran and reacted with spiro(cyclopentane-1,1'-indane)-3'-one (18.6 g, 0.1 moles) in a manner analogous to example 1. The reaction product is shaken out with benzene, the combined benzene solutions are dried with anhydrous magnesium sulphate and the solvent is distilled off in vacuum. 3'-γ-methoxypropyl-spiro(cyclopentane-1,1'-indan)-3'-ol is obtained as a yellowish oil (yield 27.1 g). The crude methoxy compound is refluxed for 62 hours with 48% hydrobromic acid (50 ml) and acetic acid (100 ml). The solution is concentrated in vacuum, ether is added to the oil obtained, and then the solution is washed with water and 2 N sodium hydroxide solution. After drying with magnesium sulphate the solvent is distilled off and a brown oil is obtained, which essentially consists of 3'-γ-bromopropyl-spiro(cyclopentane-1,1'-indene). The compound can be purified by distillation in vacuum and is then obtained as a colourless oil of mp, 148° C./1 mm Hg. $n_D^{25}$=1.5769.

Crude 3'-γ-bromopropylspiro(cyclopentane-1,1'-indene) (14.6 g), pyrrolidine (50 ml) and anhydrous toluene (50 ml) are mixed and refluxed for 7 hours. The mixture is evaporated and 20.1 g of a brown oil is obtained, which is taken up in ether and water. The ether phase is extracted with 2×150 ml of diluted sulphuric acid (100 g conc. sulphuric acid to 350 ml of water). The combined aqueous phases are washed with ether, after which the solution is made alkaline with 40% sodium hydroxide. The free amine is extracted out with trichloroethylene. The extract is dried with anhydrous potassium carbonate, and then the solvent is distilled off in vacuum. A brown oil is obtained (11.8 g), which is distilled in vacuum. The pure end product 3'-γ-(1-pyrrolidinyl)propyl-spiro-cyclopentane-1,1'-indene) is obtained as the colourless oil of mp. 160°–162° C./0.9 mm Hg $n_D^{25}$=1.5540. The perchlorate forms colourless crystals, which after recrystallization from 2-propanol melts at 115° C.

EXAMPLE 8

(a)

3'-β-dimethylaminoethyl-oximino-spiro(cyclopentane-1,1'-indan)

74.5 g (0.4 moles) spiro(cyclopentane-1,1'-indan)-3'-one, 93.6 g of hydroxylammonium chloride, 172 ml of pyridine and 440 ml of ethanol are mixed and refluxed for 3 hours and then the mixture is evaporated, 500 ml of water are added and the mixture is filtered off and dried. The crude oxime obtained is recrystallized from absolute ethanol. Yield 70 g (88%). Colourless crystals of 3'-hydroxyimino-spiro(cyclopentane-1,1'-indan) which melt at 102° C.

To a solution of 0.77 g (0.033 gram atoms) of sodium in 150 ml of absolute/ethanol there are added in portions 6 g (0.03 moles) 3'-hydroxyimino-spiro(cyclopentane-1,1'-indan), and then the mixture is refluxed for 1 hour and evaporated in vacuum. To the residue there are added 20 ml of dimethylformamide, of which 10 ml are distilled off in vacuum in order to eliminate remaining methanol. Another 80 ml of dimethylformamide are added and then 4.3 g (0.04 moles) of β-dimethylaminoethylchloride are added dropwise to the mixture at 25° C. Finally the mixture is heated for one hour at 100°–110° C. The hot solution is filtrated from the sodium chloride formed and evaporated to dryness in vacuum. The residue is taken up in ether and water, the ether phase is washed with water and dried with anhydrous pottassium carbonate The perchlorate is obtained if the ether solution of the amine, 3'-β-dimethyl-aminoethyl-oximino-spiro(cyclopentane-1,1'-indan), is treated with perchloric acid. After recrystallization from 2-propanol the salt melts at 136°–139° C.

In an analogous manner the following oximes are prepared from the corresponding indanones:

5'-nitro-3'-hydroxyiminospiro(cyclopentane-1,1'-indan), Mp. 162° C.

5'-chloro-3'-hydroxyiminospiro(cyclopentane-1,1'-indan). Mp. 140° C.

5'-fluoro-3'-hydroxyiminospiro(cyclopentane-1,1'-indan). Mp. 156° C.

5'-methoxy-3'-hydroxyimino(cyclopentane-1,1'-indan). Mp. 149° C.

In an analogous manner the following end product is prepared from the corresponding oxime and aminoalkyl chloride.

(b)

3'-γ-dimethylaminopropyl-oximino-spiro(cyclopentane-1,1'-indan).

Hydrochloride, m.p. 186°–187° C.

EXAMPLE 9

(a)

5'-chloro-3'-β-dimethylaminoethyl-oximino-spiro(cyclopentane-1,1'-indan)

5.9 g (0.025 moles) 5'-chloro-3'-hydroxyimino-spiro(cyclopentane-1,1'-indan) are dissolved in 150 ml of dimethylformamide at room temperature under agitation. 2.9 g (0.066 moles) of 55% sodium hydride (dispersed in oil) are added in portions to the solution, which is then agitated for 10 minutes at room temperature. 5.1 g (0.035 moles) of dimethylaminoethyl chloride hydrochloride are added in portions to the mixture, which is then stirred for another ten minutes at room temperature and finally for 2 hours at 100°–105° C. The sodium chloride formed is filtered off from the hot solution, which is then evaporated. The residue is taken up in ether and water, the ether solution is washed with water, and then the amine is extracted out with 2 N hydrochloric acid. The acid extract is washed with ether and made alkaline with 40% sodium hydroxide. The free amine, 5'-chloro-3'-β-dimethylaminoethyloximino-spiro(cyclopentane-1,1'-indan), is treated with perchloric acid. After recrystallization from 2-propanol the salt melts at 134° C.

In an analogous manner there is prepared from the corresponding fluorosubstituted compound (b)
5'-fluoro-3'-β-dimethylaminoethyl-oximino-spiro(cyclopentan-1,1'-indan).

Perchlorate. Mp. 172° C.

EXAMPLE 10

N-methyl-[5'-chloro-spiro(cyclopentane-1,1'-indene)-3'-yl]acetamide

5'-chlorospiro(cyclopentane-1,1'-indan)-3'-ylidenacetic acid (10 g) is refluxed with thionylchloride (75 ml) for 48 hours, whereby the exocyclic double bond is rearranged to an endocyclic one and the acid to the corresponding acid chloride. The excess of thionylchloride is distilled off in vacuum and the crude acid chloride is dissolved in ether (100 ml) and added dropwise to an agitated solution of an excess of methylamine in ether under cooling. The mixture is kept over night and then evaporated to dryness. The residue is taken up in trichloroethylene and water. The organic phase is separated and evaporated, and then the crude N-methyl-[5'-chlorospiro(cyclopentane-1,1'-indene)-3'-yl]-acetamide is crystallized from acetonitrile. Mp. 190° C.

EXAMPLE 11

3'-β-methylaminoethyl-spiro(cyclopentane-1,1'-indene)

3'-β-methylaminoethylidene-spiro(cyclopentane-1,1'indan)-hydrochloride (26.4 g; 0.10 moles) is refluxed with 500 ml of 0.1 N hydrochloric acid for 1 hour and then cooled to about 4° C., after which the crystallized salt is filtered off, washed with ice water and dried. Mp. 250°–252° C. Yield 17.3 g (65%) of the hydrochloride of 3'-β-methylaminoethyl-spiro(cyclopentane-1,1'-indene).

Another amount of material is obtained by concentrating the mother liquor. Crystallization from 2-propanol yields a product of mp. 252°–253° C.

In a similar manner the hydrochloride of 3'-β-dimethylaminoethyl-spiro(cyclopentane-1,1'-indene) is obtained from 3'-β-dimethylaminoethylidene-spiro(cyclopentane-1,1'-indan)hydrochloride. The perchlorate is obtained if said hydrochloride is converted to the free base and precipitated with perchloric acid. After crystallization from 2-propanol/methanol the salt having a mp. of about 100° C. is obtained.

EXAMPLE 12

3'-β-methylaminoethyl-spiro(cyclopentane-1,1'-indene)

Crude 3'-β-methylaminoethylidene-spiro(cyclopentane-1,1'-indan) (10 g), prepared according to example 3 is refluxed for 1 hour with the solution of excess of hydrogen chloride in 2-propanol and cooled to room temperature. Diisopropylether is added and then the hydrochloride of 3'-β-methylaminoethyl-spiro(cyclopentane-1,1'-indene) precipitate. The salt is sucked off and recrystallized from 2-propanol.

EXAMPLE 13

3'-β-aminoethyl-spiro(cyclopentane-1,1'-indene)

Spiro(cyclopentane-1,1'-indan)-3'-ylideneacetonitrile

To a mixture of cyanoacetic acid (85 g; 1.0 moles) and spiro(cyclopentane-1,1'-indan)-3'-one (186 g; 1.0 moles) there is added piperidine (85.2 g; 1.0 moles) dropwise under agitation and cooling at such a rate that the temperature does not exceed 40°–60° C. After addition of benzene (300 ml) the mixture is refluxed for 24 hours with continuous separation of the water formed. Benzene and piperidine are distilled off under reduced pressure and the oil obtained is distilled in vacuum. At 130°–140° C./1 torr there is obtained a colourless oil consisting of the title nitrile as well as the isomer spiro(cyclopentane-1,1'-indene)-3'-ylacetonitrile and a small amount of unreacted ketone. The mixture is dissolved in hot hexane and cooled, and then spiro(cyclopentane-1,1'-indan)-3'-ylideneacetonitrile crystallizes as colourless crystals of mp 82° C.

(b) Isomerisation of a nitrile mixture from the mother liquor

The solvent is eliminated from the mother liquor from (a) and then an oil is obtained, which consists of about 70% of spiro(cyclopentane-1,1'-indene)-3'-ylacetonitrile and of 30% spiro(cyclopentane-1,1'-indan)-3'-ylideneacetonitrile as well as unreacted ketone.

110 g of such a mixture is dissolved in ethanol (300 ml). The nitrile (0.6 g) is added and the mixture is refluxed for 48 hours. After evaporation of the alcohol and treatment with water there is obtained an oil which is dissolved in ether, washed, dried and evaporated. After this isomerisation the product consists almost exclusively of spiro(cyclopentane-1,1'-indan)-3'-ylideneacetonitrile as well as ketone, and the nitrile is separated from this mixture by crystallization from hexane as described in example 13a.

(c)
3'-β-aminoethylidene-spiro(cyclopentane-1,1'-indan)

A solution of spiro(cyclopentane-1,1'-indan)-3'-ylideneacetonitrile (10.5 g; 0.05 moles) in anhydrous ether (100 ml) is added dropwise under agitation to lithium aluminum hydride (2.5 g; 0.066 moles) suspended in ether (200 ml). After boiling for 3 hours the mixture is cooled to room temperature and the excess of hydride is decomposed by dropwise addition of a saturated sodium sulphate solution. The precipitate obtained is filtered off and washed with ether. The ether solutions are shaken with 2 N hydrochloric acid. The acid extracts are concentrated to a small volume in vacuum (bath temperature below 40° C.) and the amine hydrochloride is precipitated by treatment with conc. hydrochloric acid in the cooled. Yield 10.6 g (85%). Recrystallization from 2-propanol yields colourless crystals of mp. 190° C. identical with the product prepared according to example 3g.

(d) 3'-β-aminoethyl-spiro(cyclopentane-1,1'-indene)

3'-β-aminoethylidene-spiro(cyclopentane-1,1'-indan)-hydrochloride (4.0 g; 0.016 moles) is boiled for 4 hours with a mixture of water (100 ml) and conc. hydrochloric acid (15 ml). Upon cooling of the solution 3.8 g (95%) of the hydrochloride of 3'-β-aminoethyl-spiro(-cyclopentane-1,1'-indene) crystallizes. Mp. 256°–257° C. after recrystallization from 2-propanol.

An identical product is obtained if spiro(cyclopentane-1,1'-indene)-3'-ylacetonitrile is reduced with lithium aluminum-hydride as described in example 13c.

What we claim is:

1. A novel indan derivative of the general structure

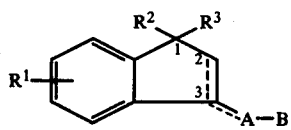

wherein:

R¹ is selected from the group consisting of hydrogen, fluorine, chlorine, and alkoxy radicals having 1 to 3 carbon atoms;

R² and R³ are selected from the group consisting of alkyl radicals having 1 to 3 carbon atoms which, together with the carbon atom by which they are connected to the indan ring, may form a ring;

A is an alkyl or alkylidene group having from 2 to 4 carbon atoms or an alkyl or alkylidene group of from 2 to 4 carbon atoms having an alkyl side branch thereon;

B is an amino group of the formula

wherein R⁴ and R⁵ each signify hydrogen or alkyl groups of from 1 to 4 carbon atoms;

the broken line extending between the 2 and 3 positions of the indan nucleus and substituent A signifies a double bond in either the endo- or exo-position;

or the amine oxide or a pharmaceutically acceptable salt of said indan derivative.

2. A compound according to claim 1 wherein R² and R³ each signify a methyl group.

3. A compound according to claim 1 wherein R² and R³, together with the carbon atoms by which they are bonded to the indan ring, form a cyclopentane ring.

4. A compound according to claim 1 wherein R¹ is a, fluorine or chlorine.

5. The compound according to claim 1 3'-β-aminoethyl-spiro(cyclopentane-1,1'-indene).

6. The compound according to claim 1 3'-β-methylaminoethyl-5'-chloro-spiro(cyclopentane-1,1'-indene).

7. The compound according to claim 1 3'-β-methylaminoethyl-5'-fluoro-spiro(cyclopentane-1,1'-indene).

8. The compound according to claim 1 3'-β-dimethylaminoethyliden-5'-chloro-spiro(cyclopentane-1,1'-indan).

9. The compound according to claim 1 3'-β-dimethylaminoethyl-5'-fluoro-spiro(cyclopentane-1,1'-indene).

10. The compound according to claim 1 1,1-dimethyl-3-γ-dimethylaminopropylindene.

11. The compound according to claim 1 3'-γ-dimethylaminopropyl-spiro(cyclohexane-1,1'-indene).

12. 3'-β-methylaminoethyl-spiro(cyclopentane-1,1'-indene).

13. The compound according to claim 1 3'-β-dimethylaminoethyl-spiro(cyclopentane-1,1'-indene).

14. The compound according to claim 1 3'-γ-dimethylaminopropyl-spiro(cyclopentane-1,1'-indene)N-oxid.

15. The compound according to claim 1 3'-γ-dimethylaminopropyl-spiro(cyclohexane-1,1'-indene)N-oxid.

16. The compound according to claim 1 3'-γ-methylaminopropyl-spiro(cyclopentane-1,1'-indene).

17. The compound according to claim 1 3'-γ-dimethylaminopropyl-5'-fluoro-spiro(cyclopentane-1,1'-indene).

18. The compound according to claim 1 3'-α-methyl-β-dimethylaminoethyl-spiro(cyclopentane-1,1'-indene).

19. The compound according to claim 1 3'-β-aminoethylidene-spiro(cyclopentane-1,1'-indan).

20. The compound according to claim 1 3'-β-methylaminoethylidene-spiro(cyclopentane-1,1'-indan).

21. The compound according to claim 1 3'-β-dimethylaminoethylidene-spiro(cyclopentane-1,1'-indan).

* * * * *

UNITED STATES PATENT AND TRADEMARK OFFICE
CERTIFICATE OF CORRECTION

PATENT NO. : 4,172,093
DATED : October 23, 1979
INVENTOR(S) : Barbro K. Goransson-Dahlander et al.

It is certified that error appears in the above—identified patent and that said Letters Patent is hereby corrected as shown below:

Col. 1, line 62, "indane" should be -- indan --;

Col. 5, lines 45-46, "togehter" should be -- together --;

Col. 6, line 3, "freee" should be -- free --;

Col. 6, line 37, "process" should be -- possess --;

Col. 9, line 4, "disintergrates" should be -- disintegrates --;

Col. 9, line 5, "disintergrated" should be -- disintegrated --;

Col. 9, line 64, "disintergrated" should be -- disintegrated --;

Col. 12, line 6, "as" should be -- is --;

Col. 16, line 2, preceding "melt", insert -- , --; and

Col. 18, line 61, following "cooled" and before the period, insert -- condition --.

UNITED STATES PATENT AND TRADEMARK OFFICE
CERTIFICATE OF CORRECTION

PATENT NO. : 4,172,093
DATED : October 23, 1979
INVENTOR(S) : Barbro K. Goransson-Dahlander et al.

It is certified that error appears in the above—identified patent and that said Letters Patent is hereby corrected as shown below:

First Page, Item 30, "Mar. 24, 1872" should read --Mar. 24, 1972--;

Col. 6, lines 20-27, delete the following formula:

" 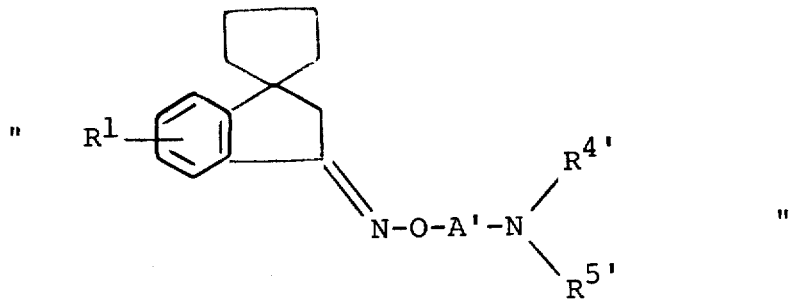 "

and substitute the following formula:

-- 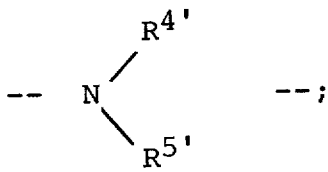 --;

Col. 6, line 68, "completion" should read --complete--;
Col. 7, first line of table, after "Antagonism", the ":" should read --%--;
Col. 7, first item under Col. A in the table, "-(CH2)3" should read --  -(CH2)3-  --;

UNITED STATES PATENT AND TRADEMARK OFFICE
CERTIFICATE OF CORRECTION

PATENT NO. : 4,172,093

DATED : October 23, 1979

INVENTOR(S) : Barbro K. Goransson-Dahlander et al.

It is certified that error appears in the above—identified patent and that said Letters Patent is hereby corrected as shown below:

Col. 7, table, Col. headed "40", item fourth from bottom marked "10" should read --100--;
Col. 7, line 37, after "have", insert --been--;
Col. 8, line 2, "1917 g" should read --19.7 g--;
Col. 9, line 29, "liquid" should read --liquor--;
Col. 16, line 2, "melts" should read --melt--;
Col. 16, line 18, "absolute/ethanol" should read --absolute ethanol--; and
Col. 18, line 8, before "Spiro" insert --(a)--.

Signed and Sealed this

Fourteenth Day of October 1980

[SEAL]

*Attest:*

SIDNEY A. DIAMOND

*Attesting Officer*

*Commissioner of Patents and Trademarks*